United States Patent
Tochterman et al.

(10) Patent No.: US 10,993,628 B2
(45) Date of Patent: May 4, 2021

(54) DEVICES, SYSTEMS, AND METHODS FOR VESSEL ASSESSMENT

(71) Applicant: Volcano Corporation, San Diego, CA (US)

(72) Inventors: Andrew Tochterman, Carlsbad, CA (US); David Anderson, Temecula, CA (US); Fergus Merritt, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1054 days.

(21) Appl. No.: 14/522,952

(22) Filed: Oct. 24, 2014

(65) Prior Publication Data

US 2015/0119705 A1    Apr. 30, 2015

Related U.S. Application Data

(60) Provisional application No. 61/895,909, filed on Oct. 25, 2013.

(51) Int. Cl.
*A61B 5/0215* (2006.01)
*A61B 6/00* (2006.01)
*A61B 6/03* (2006.01)

(52) U.S. Cl.
CPC .......... *A61B 5/02158* (2013.01); *A61B 6/463* (2013.01); *A61B 6/481* (2013.01); *A61B 6/504* (2013.01); *A61B 6/032* (2013.01)

(58) Field of Classification Search
None
See application file for complete search history.

(56) References Cited

U.S. PATENT DOCUMENTS

| 5,108,369 A * | 4/1992 | Ganguly | A61B 5/0215 604/102.02 |
| 6,565,514 B2 * | 5/2003 | Svanerudh | A61B 5/0215 600/485 |

(Continued)

FOREIGN PATENT DOCUMENTS

| WO | 2006076409 A2 | 7/2006 |
| WO | 2010030882 A1 | 3/2010 |
| WO | WO 2013-028612 | 2/2013 |

OTHER PUBLICATIONS

Nam et al. "Funcation SYNTAX score for risk assessment in multivessel coronary artery disease". Journal of the American College of Cardiology, 2011, vol. 58, No. 12, pp. 1211-1218.*

(Continued)

*Primary Examiner* — Pascal M Bui Pho
*Assistant Examiner* — Yi-Shan Yang

(57) ABSTRACT

Devices, systems, and methods for visually depicting a vessel and evaluating risk associated with a condition of the vessel are disclosed. In one embodiment, a method of evaluating a vessel of a patient includes obtaining physiology measurements from a first instrument and a second instrument positioned within the vessel of the patient while the second instrument is moved longitudinally through the vessel from a first position to a second position and the first instrument remains stationary within the vessel; outputting the physiology measurements and an image of the vessel on a display, the output image including visualizations based on the obtained physiology measurements; and evaluating whether to perform to surgical procedure based on the physiology measurements and the image of the vessel.

23 Claims, 12 Drawing Sheets

(56) References Cited

U.S. PATENT DOCUMENTS

| | | | |
|---|---|---|---|
| 7,930,014 B2 | 4/2011 | Huennekens et al. | |
| 8,548,778 B1* | 10/2013 | Hart | A61B 6/466 703/6 |
| 2004/0002660 A1 | 1/2004 | Mielekamp | |
| 2006/0052700 A1* | 3/2006 | Svanerudh | A61B 5/0215 600/438 |
| 2006/0106321 A1 | 5/2006 | Lewinsky et al. | |
| 2006/0241465 A1* | 10/2006 | Huennekens | A61B 6/504 600/458 |
| 2010/0234698 A1* | 9/2010 | Manstrom | A61B 5/02007 600/301 |
| 2012/0041319 A1* | 2/2012 | Taylor | G06T 7/11 600/508 |
| 2012/0063663 A1 | 3/2012 | Kawasaki | |
| 2012/0136244 A1* | 5/2012 | Manstrom | A61M 5/007 600/431 |
| 2012/0243764 A1* | 9/2012 | Dey | A61B 6/032 382/131 |
| 2012/0265283 A1 | 10/2012 | Mack et al. | |
| 2013/0046190 A1* | 2/2013 | Davies | A61B 5/742 600/486 |
| 2013/0131523 A1* | 5/2013 | Suchecki | A61B 5/02007 600/486 |
| 2014/0187920 A1 | 7/2014 | Millett et al. | |
| 2015/0161790 A1* | 6/2015 | Takahashi | A61B 6/507 600/424 |

OTHER PUBLICATIONS

International Searching Authority/United States Patent Office, "Notification of Transmittal of the International Search Report and the Written Opinion of the International Searching Authority, or the Declaration," for PCT/US2014/062084, dated Jan. 26, 2015, 13 pages.

Chang-Wook Nam et al "Function SYNTAX Score for Risk Assessment in Multivessel Coronary Artery Disease", Journal of the American College of Cardiology, vol. 58, No. 12, Jun. 2011.

U.S. Appl. No. 14/335,603, filed Jul. 18, 2004, Joe Burnett et al.

Chang-Wook Nam et al., Functional SYNTAX Score for Risk Assessment in Multivessel Coronary After Disease, Journal of American College of Cardiology 2011; 58 (12): 1211-1218.

Hills, L. David et al "2011 ACCF/AHA Guideline for Coronary Artery Bypass Graft Surgery", Journal of the American College of Cardiology, vol. 58, No. 24, Dec. 2011, pp. 123-210.

Akasaka, Takashi "Application of a Pressure Guide Wire Combined with Thermography in the Assessment of coronary Stenotic Lesions", Japanese Society for Medical and Cardiology, vol. 43, No. 1, 2005, pp. 24-31.

* cited by examiner

DEVICES, SYSTEMS, AND METHODS FOR VESSEL ASSESSMENT

CROSS-REFERENCE TO RELATED APPLICATION

The present application claims the benefit of the filing date of U.S. Provisional Application No. 61/895,909 filed Oct. 25, 2013. The entire disclosure of this provisional application is incorporated herein by this reference.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include percutaneous coronary intervention (PCI or angioplasty), stenting, or coronary artery bypass graft (CABG) surgery. As with all medical procedures, certain risks are associated with PCI, stenting, and CABG procedures. In order for a surgeon to make a better-informed decision regarding treatment options, additional information about the risk and likelihood of success associated with the treatment options is needed.

A patient's vasculature can be visualized using angiography. However, the locations of stenoses in a vessel can be difficult to visualize in a black and white angiographic image. Moreover, the severity of stenosis can also be better understood when efficiently visualized in relation to an angiographic image. Further, a more complete diagnosis of the patient can be made when the effects of both focal and diffuse stenoses are evaluated.

Accordingly, there remains a need for improved devices, systems, and methods for assessing the severity of a blockage in a vessel and, in particular, a stenosis in a blood vessel. In that regard, there remains a need for improved devices, systems, and methods for providing visual depictions of vessel that allow assessment of the vessel and, in particular, any stenosis or lesion of the vessel. Further, there remains a need for improved devices, systems, and methods of objectively evaluating risk associated with and likelihood of success for one or more available treatment options for the vessel.

SUMMARY

Embodiments of the present disclosure are configured to assess the severity of a blockage (or multiple blockages) in a vessel and, in particular, a stenosis in a blood vessel. In some particular embodiments, the devices, systems, and methods of the present disclosure are configured to provide visual depictions of a vessel that allow assessment of the vessel and, in particular, any stenosis or lesion of the vessel. Further, in some embodiments the devices, systems, and methods of the present disclosure are configured to allow planning of one or more treatment options for the vessel based on objective measures of risk and/or success.

In one embodiment, a method of evaluating a vessel of a patient are provided. The method includes obtaining physiology measurements from a first instrument and a second instrument positioned within the vessel of the patient while the second instrument is moved longitudinally through the vessel from a first position to a second position and the first instrument remains stationary within the vessel; outputting the physiology measurements and an image of the vessel on a display, the output image including visualizations based on the obtained physiology measurements; and evaluating whether to perform to a surgical procedure based on the physiology measurements and the image of the vessel.

In some implementations, the visualizations include markings representative of a location of obtained physiology measurements from the first and second instruments. In some implementations, the markings are movable along the image of the vessel. In some implementations, the visualizations include indicators representative of a region of interest based on the obtained pressure measurements from the first and second instruments. In some implementations, the indicators are movable along the image of the vessel. In some implementations, the visualizations include numerical values of a pressure ratio of the obtained pressure measurements from the first and second instruments. In some implementations, the visualizations include a heat map representative of a pressure ratio of the obtained pressure measurements from the first and second instruments. In some implementations, a first visual characteristic of the heat map is associated with pressure ratios above a threshold value and a second visual characteristic of the heat map is associated with pressure ratios below the threshold value. In some implementations, the first visual characteristic of the heat map is a first color and the second visual characteristic of the heat map is a second color visually distinguishable from the first color. In some implementations, the image is an extravascular image. In some implementations, the extravascular image is at least one of a two dimensional angiographic image, a three dimensional angiographic image, and a computed tomography angiographic (CTA) image. In some implementations, the surgical procedure is at least one of coronary artery bypass graft and a percutaneous coronary intervention. In some implementations, the method further includes calculating a risk score associated with the obtained physiology measurements; outputting the risk score on the display; and evaluating whether to perform to surgical procedure based on the risk score. In some implementations, calculating a risk score includes providing the physiology measurements to a risk calculator, wherein the risk calculator includes a calculator for determining at least one of a SYNTAX score, a fractional flow reserve (FFR)-guided SYNTAX score (referred to as a functional SYNTAX score), an indication of perfusion benefit, and an indication of graft patency; and calculating the risk score with the risk calculator using at least one of the physiology measurements and a patient history. In some implementations, calculating a risk score includes providing the physiology measurements into an algorithm for predicting the benefits of perfusion resulting from placement of a coronary bypass graft.

In one embodiment, a system for evaluating a vessel of a patient is provided. The system includes a first instrument sized and shaped for introduction into the vessel of the patient; a second instrument sized and shaped for introduction into the vessel of the patient; a processing system in communication with the first and second instruments, the processing unit configured to: obtain physiology measurements from the first and second instruments while the second instrument is moved longitudinally through the vessel of the patient from a first position to a second position while the first instrument is maintained in a fixed longitudinal position with respect to the vessel; output the physiology measurements and an image of the vessel on a display in communication with the processing system, the output image including visualizations based on the obtained physiology measurements; and evaluate whether to perform a surgical procedure based on the physiology measurements and the image of the vessel.

In some implementations, the visualizations include markings representative of a location of obtained physiology measurements from the first and second instruments. In some implementations, the markings are movable along the image of the vessel. In some implementations, the visualizations include indicators representative of a region of interest based on the obtained pressure measurements from the first and second instruments. In some implementations, the indicators are movable along the image of the vessel. In some implementations, the visualizations include numerical values of a pressure ratio of the obtained pressure measurements from the first and second instruments. In some implementations, the visualizations include a heat map representative of a pressure ratio of the obtained pressure measurements from the first and second instruments. In some implementations, a first visual characteristic of the heat map is associated with pressure ratios above a threshold value and a second visual characteristic of the heat map is associated with pressure ratios below the threshold value. In some implementations, the first visual characteristic of the heat map is a first color and the second visual characteristic of the heat map is a second color visually distinguishable from the first color. In some implementations, the image is an extravascular image. In some implementations, the extravascular image is at least one of a two dimensional angiographic image, a three dimensional angiographic image, and a computed tomography angiographic (CTA) image. In some implementations, the surgical procedure is at least one of coronary artery bypass graft and a percutaneous coronary intervention. In some implementations, the processing unit is further configured to calculate a risk score associated with the obtained physiology measurements; output the risk score on the display; and evaluate whether to perform to surgical procedure based on the risk score. In some implementations, calculating a risk score includes providing the physiology measurements to a risk calculator, wherein the risk calculator includes a calculator for determining at least one of a SYNTAX score, a fractional flow reserve (FFR)-guided SYNTAX score (functional SYNTAX score), an indication of perfusion benefit, and an indication of graft patency; and calculating the risk score with the risk calculator using at least one of the physiology measurements and a patient history. In some implementations, calculating a risk score includes providing the physiology measurements into an algorithm for predicting the benefits of perfusion resulting from placement of a coronary artery bypass graft.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
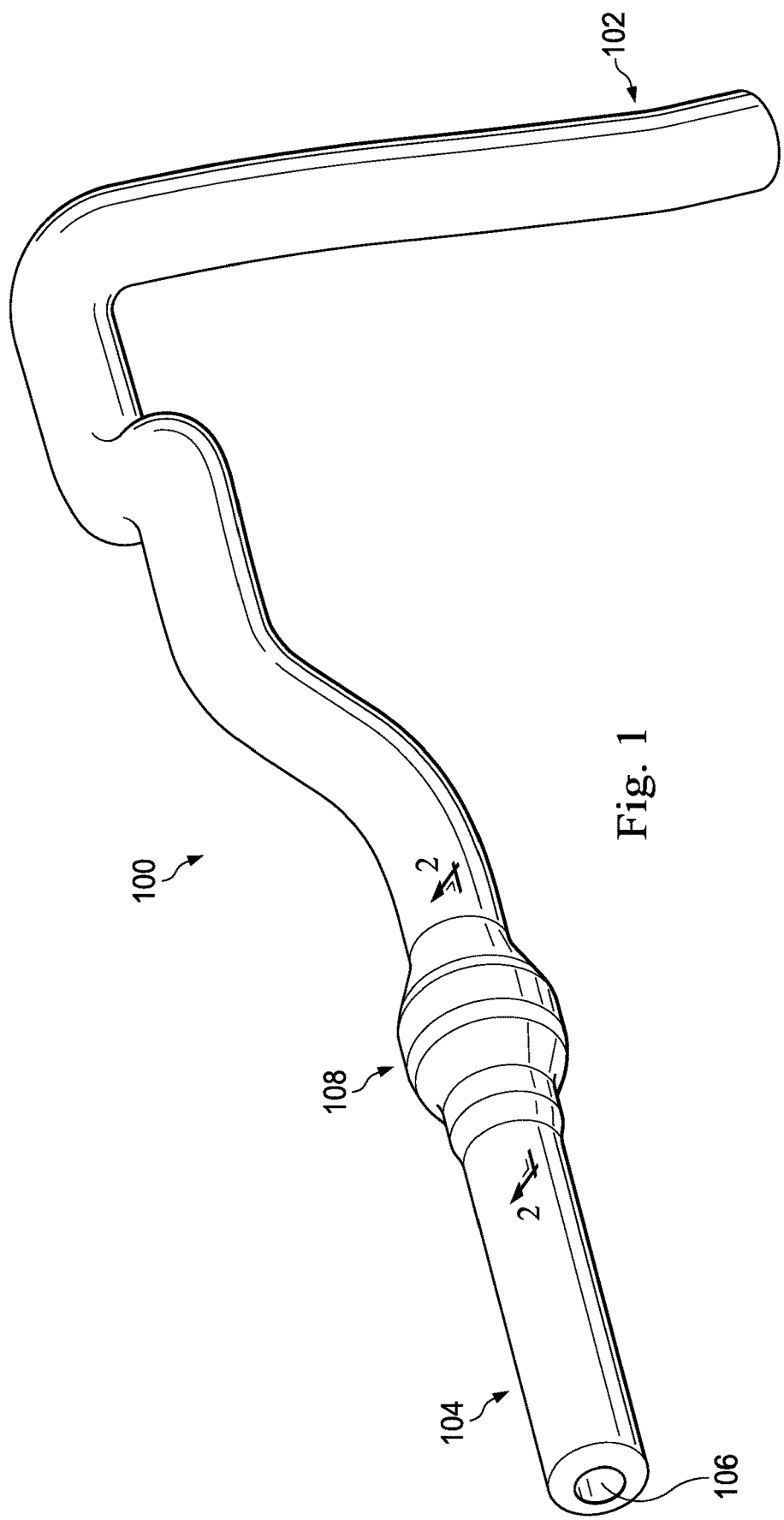
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Physiological data and the coronary angiogram typically behave as complementary, yet segregated sources of information. The coronary angiogram has been used to make treatment decisions. More recently, physiological data (including, but not limited to, pressure and/or flow measurements, both at Hyperemia and rest) have shown that better decisions can be made based on the severity of a blockage by measuring the change in underlying physiological conditions from the beginning of a target artery to the end. Treating a patient based on the severity of this change or delta has shown to improve outcomes and reduce waste from unnecessary procedures. In one or more aspects of the present disclosure, the physiological data, as collected real-time, is linked to a schematic of the coronary arteries or an angiogram. The data are depicted in a way that allows a clinician to interact and assess where severity changes, by sliding markings as placed on the image of the vessel and correlated with the collected physiological data. One or more embodiments described herein are also able automatically to make updates based on the collected data to a risk calculator such as a Functional Syntax Score or a model for predicting changes in perfusion to create a Coronary Artery Bypass Graft ("CABG") Map.

One aspect of the present disclosure includes super-imposing real-time collected pressure and/or flow data (or other physiologic data) onto an angiogram, or a schematic of anatomy and representing the data in a way that helps a clinician determine how/where to intervene (including but not limited to CABG mapping and PCI planning). One aspect of the present disclosure includes using the pressure, flow or other physiologic data with a computational algorithm to predict probabilities of graft patency and perfusion improvement during coronary artery bypass grafting (CABG). One aspect of the present disclosure includes interacting with super-imposed physiologic data to isolate "regions of interest" where severity of physiologic data changes substantially for the purposes of determining how/where to intervene. One aspect of the present disclosure includes using the physician-determined regions of interest to auto-calculate a risk score including but not limited to a Functional Syntax Score. Whether to perform to surgical procedure can be evaluated based on one or more of physiology measurements, an image of the vessel with one or more visualizations, and relevant risk & perfusion calculations.

In some embodiments, PCI planning is facilitated by the graphical overlay of physiologic data and the ability to add/delete and drag markings that allow the user to size and isolate blockages. Using the guide catheter and/or the guide wire as a calibrated and known length permits these markings, and co-registered physiologic data to estimate lesion lengths. These data can be inputted into a risk calculator including but not limited to a Functional Syntax Score. The use of the markings, length, and physiologic data permit the interventionalist to plan a percutaneous coronary intervention whereby the number of stents, and length of stents can be estimated.

In some embodiments, CABG mapping is facilitated by the graphical overlay of physiologic data and the ability to add/delete and drag the markings that allow the user to size and isolate the blockages. In planning a bypass surgery (CABG), the data allows the physician to identify where on the artery the disease starts and stops. This results in a CABG map, where the ideal placement of a graph can be determined and the prediction of graft patency and perfusion benefit can be identified to support decision making. The benefit of this is optimizing outcomes like graft patency and reducing costs like unnecessary grafting and time.

Figure 2:
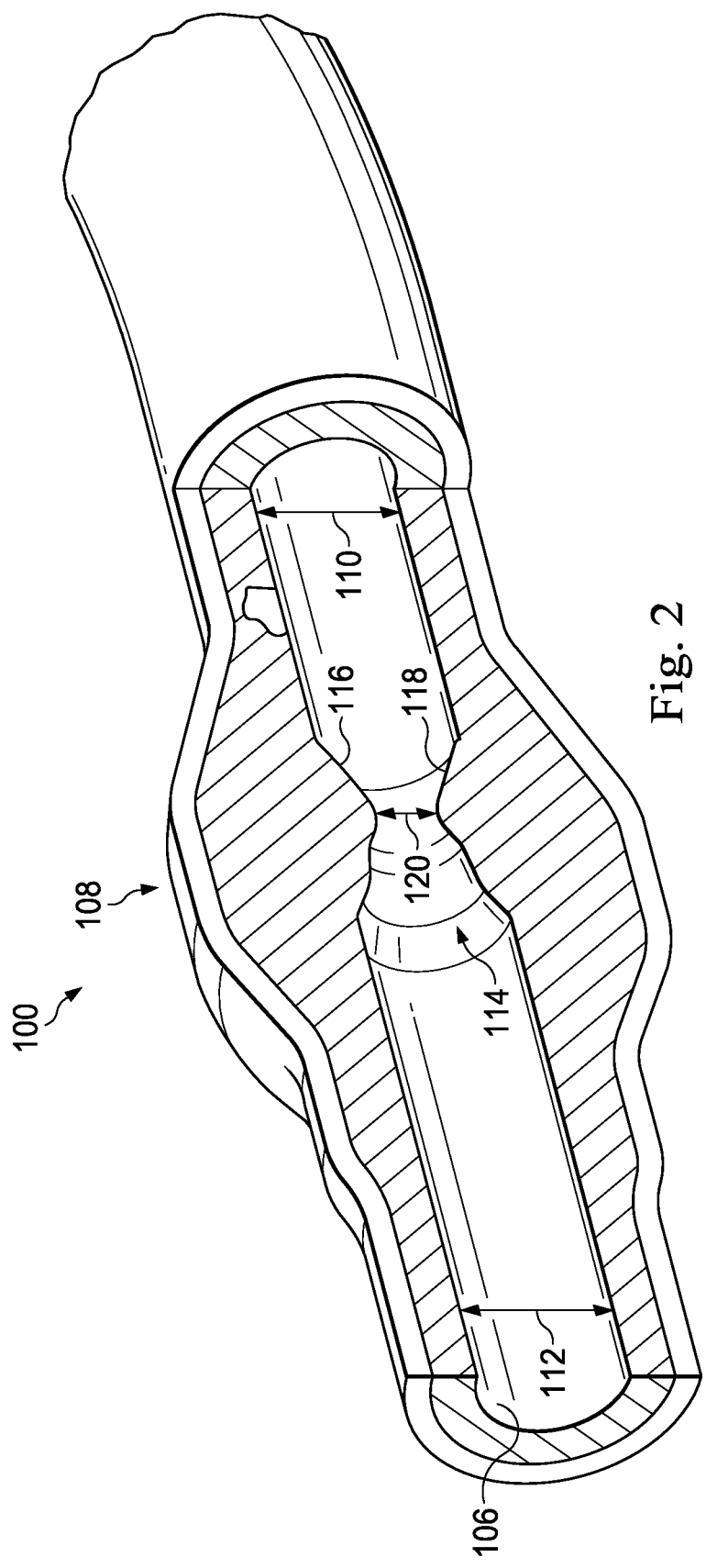
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
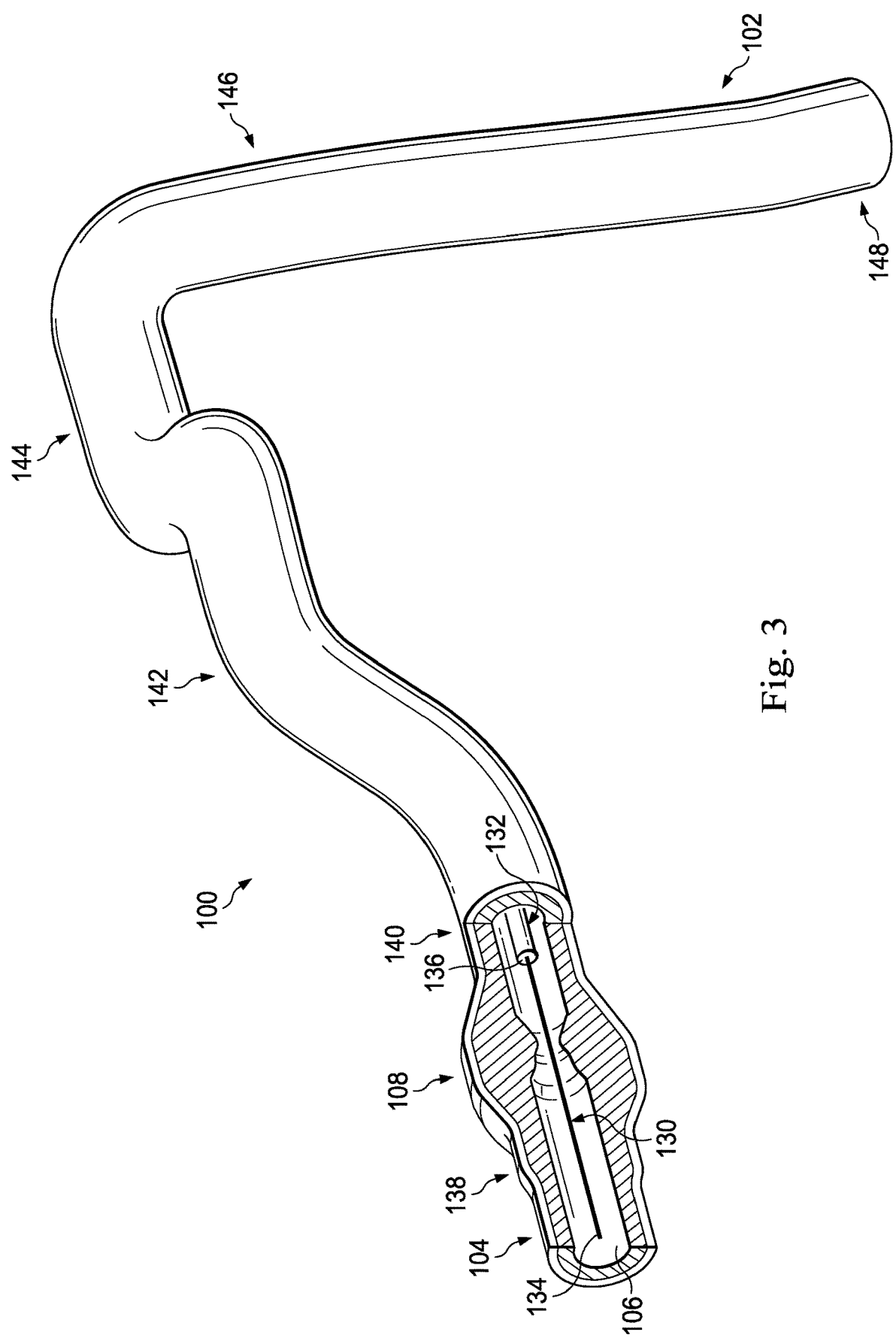
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM® Sensis, Mennen Horizon XVu, and Philips Xper® IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guidewire relative to the pressure reading of a guide catheter. In that regard, because FFR is calculated as the ratio of the pressure measurement obtained by the guidewire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 4:
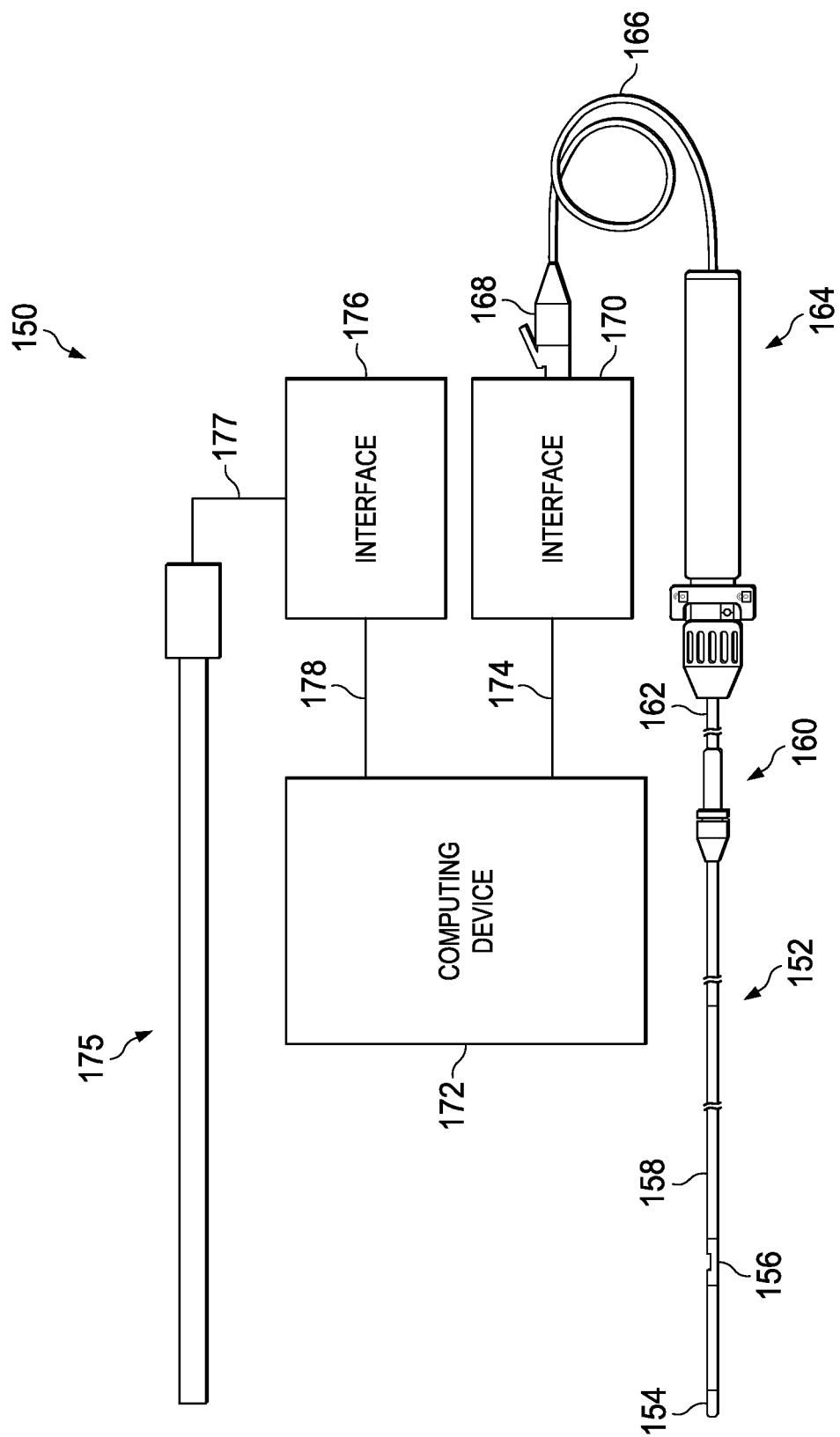
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM® Sensis, Mennen Horizon XVu, and Philips Xper® IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include FFR, Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc.

In some embodiments, the diagnostic information can include angiographic images and/or other two-dimensional or three-dimensional depictions of a patient's vasculature. The diagnostic information and/or data obtained by instruments 130, 132, 152, and/or 175 are correlated or co-registered to angiographic image(s) and/or other two-dimensional or three-dimensional depictions of a patient's vasculature. Co-registration can be completed using techniques disclosed in U.S. Pat. No. 7,930,014, issued on Apr. 19, 2011, titled "VASCULAR IMAGE CO-REGISTRATION," which is hereby incorporated by reference in its entirety, based on the known pullback speed/distance, based on a known starting point, based on a known ending point, and/or combinations thereof. In some embodiments, diagnostic information and/or data is correlated to vessel images using techniques similar to those described in U.S. Patent Publication No. 2014/0187920 A1, titled "DEVICES, SYSTEMS, AND METHODS FOR ASSESSMENT OF VESSELS" and published on Jul. 3, 2014, which is hereby incorporated by reference in its entirety. In some embodiments, co-registration and/or correlation can be completed as described in U.S. patent application Ser. No. 14/335,603, titled "DEVICES, SYSTEMS, AND METHODS FOR ASSESSMENT OF VESSELS" and filed on Jul. 18, 2014, which is hereby incorporated by reference in its entirety.

Figure 5:
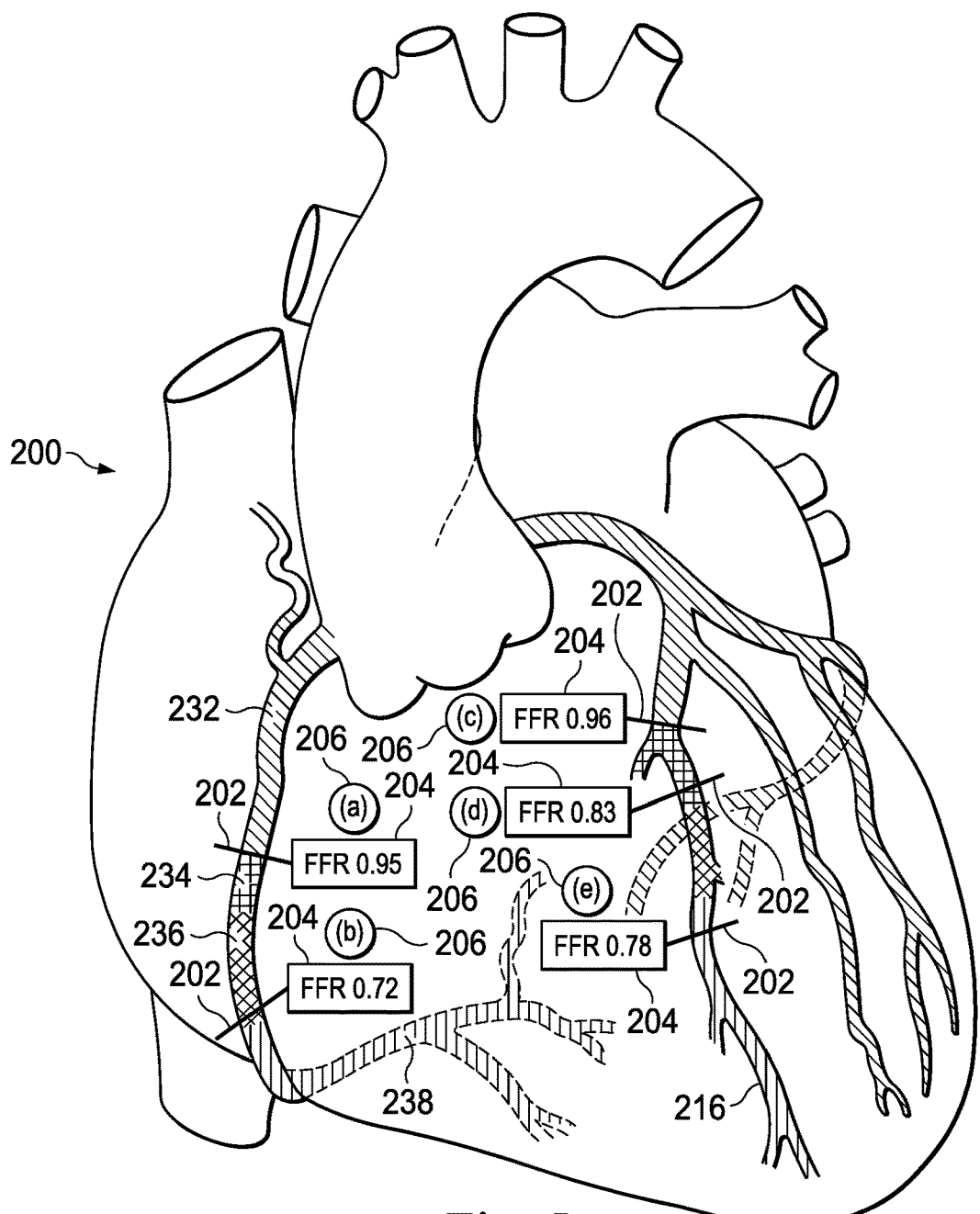
FIG. 5 is an annotated version of a stylized image of a patient's vasculature according to an embodiment of the present disclosure.
Figure 6:
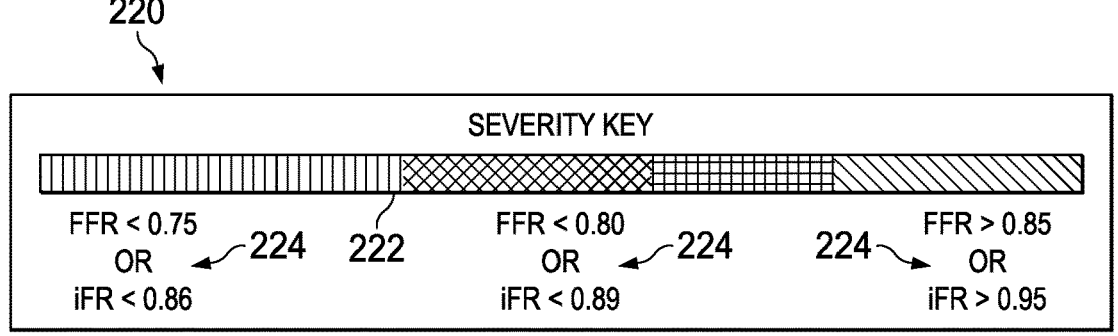
FIG. 6 is a visual depiction of an index of the severity of stenoses according to an embodiment of the present disclosure.
Figure 7:
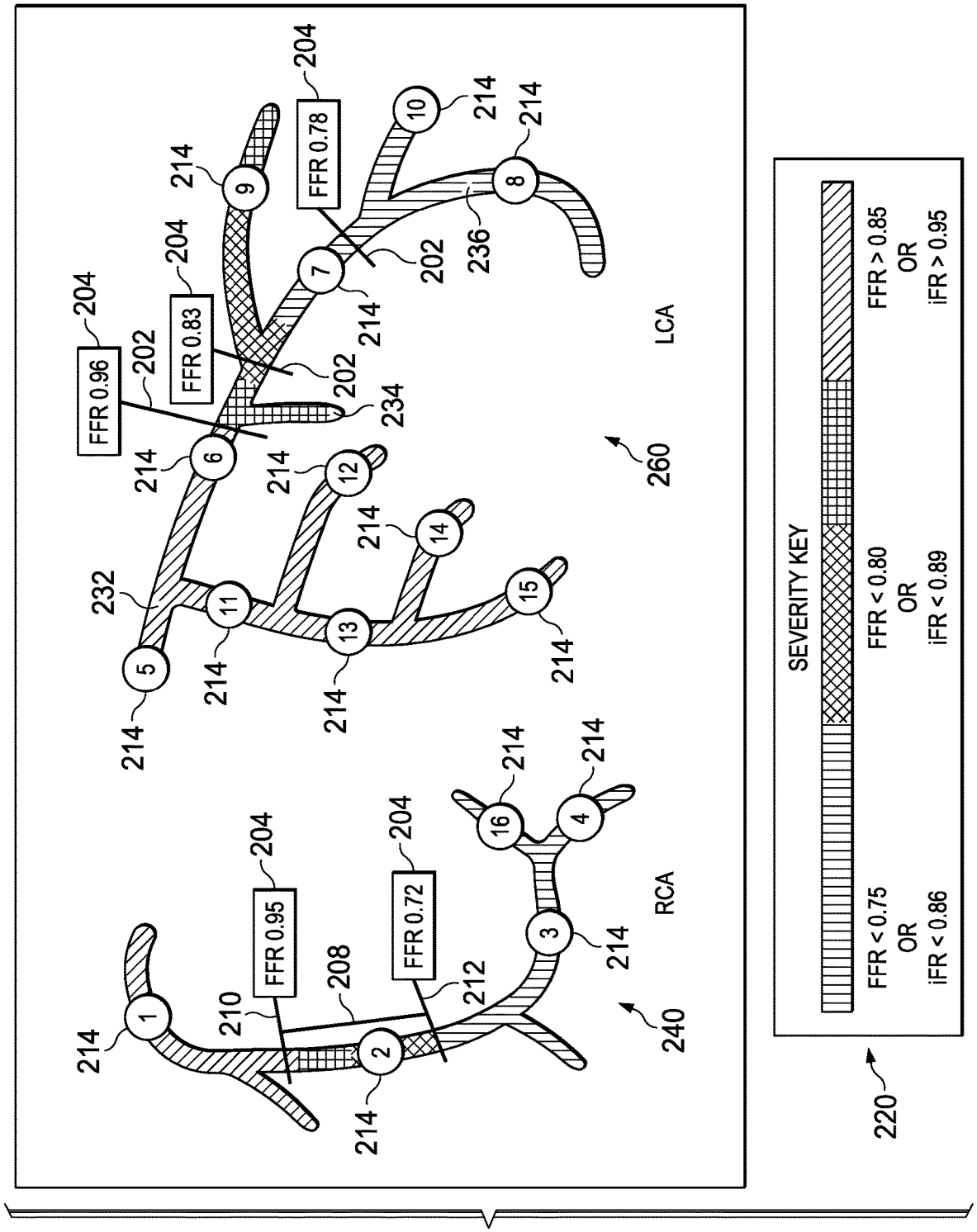
FIG. 7 is an annotated version of a stylized image of a vessel according to another embodiment of the present disclosure.
Figure 8:
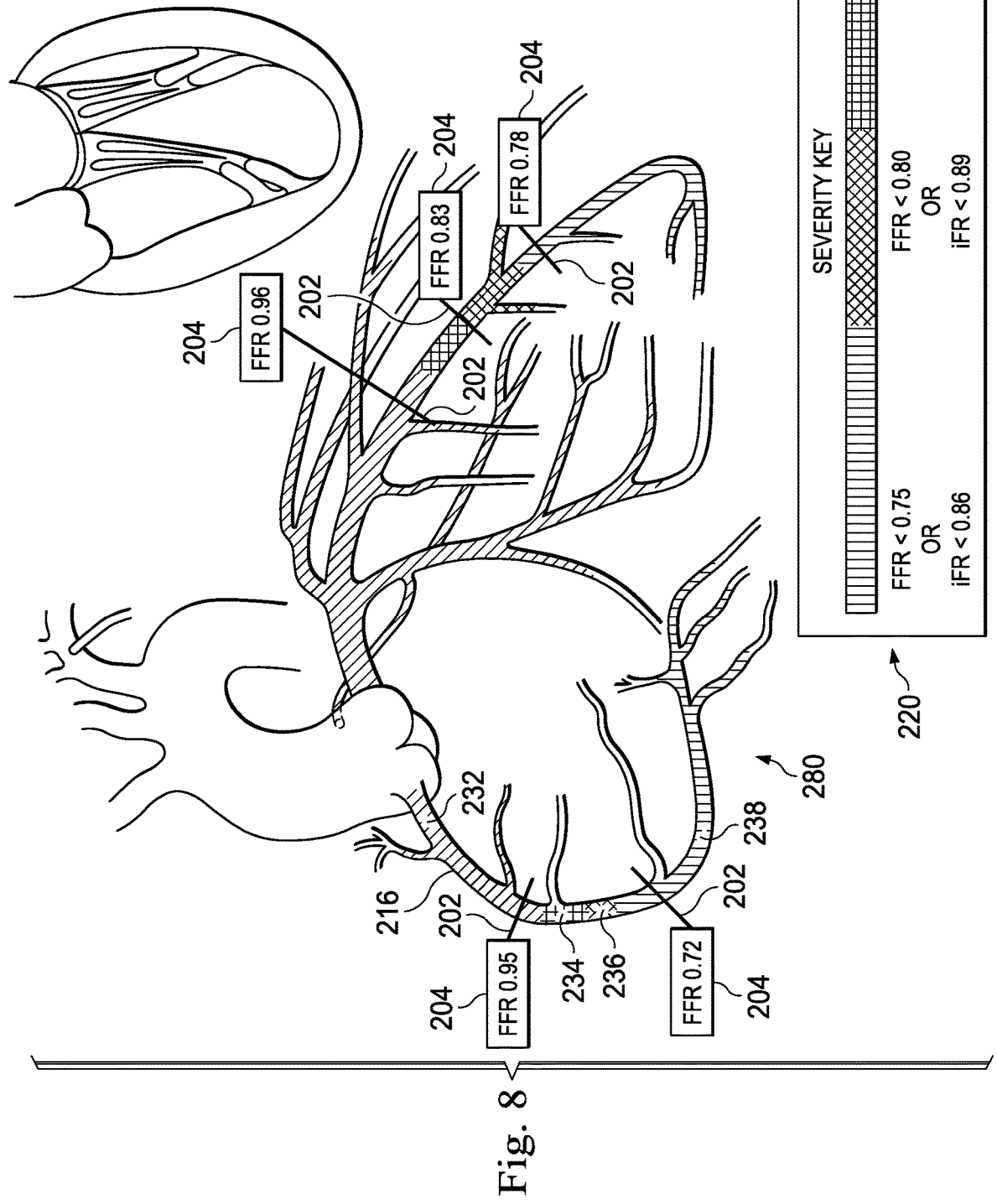
FIG. 8 is an annotated version of a stylized image of a vessel according to another embodiment of the present disclosure.
Figure 9:
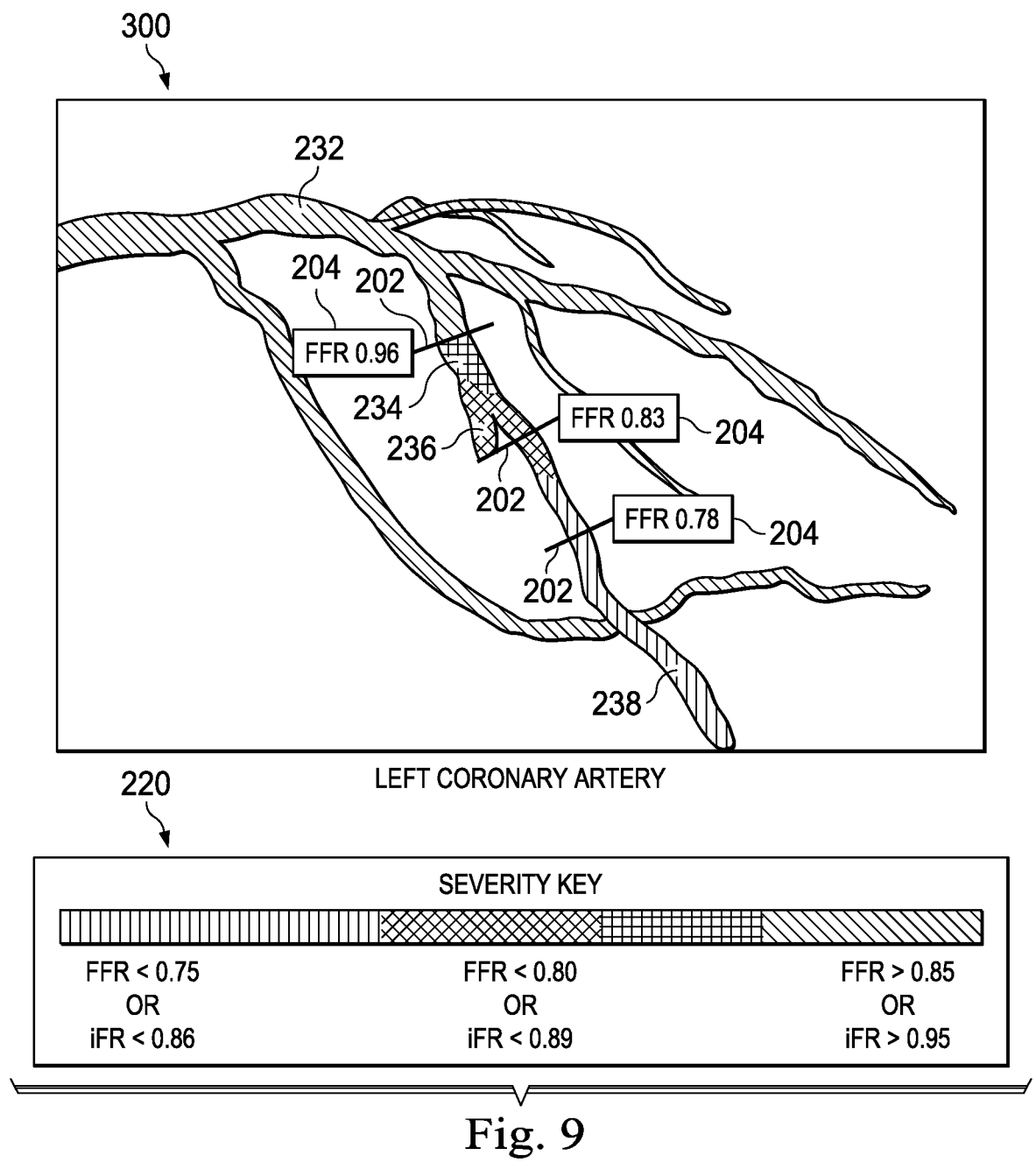
FIG. 9 is an annotated version of an angiographic image of a vessel according to an embodiment of the present disclosure.
Figure 10:
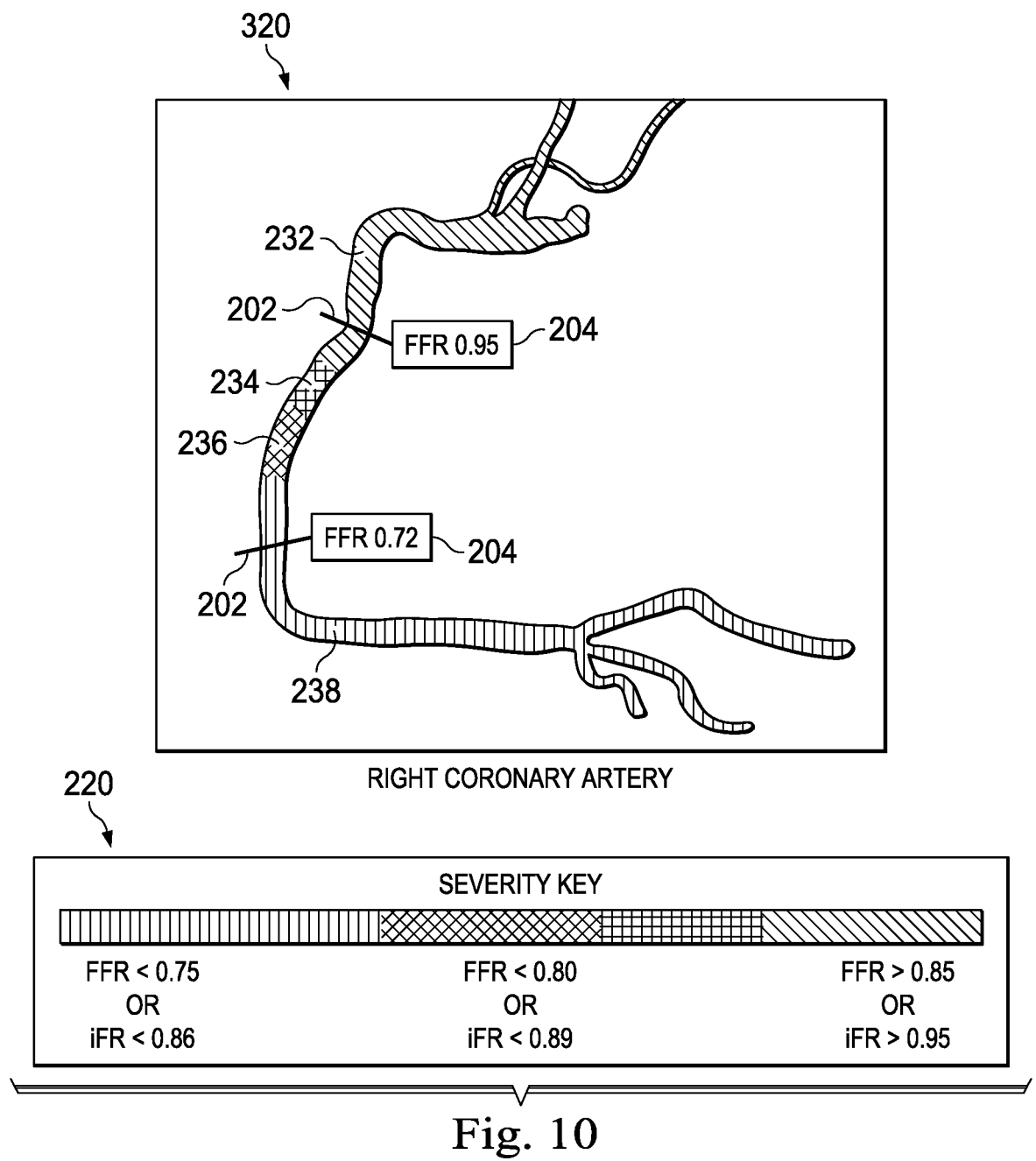
FIG. 10 is an annotated version of an angiographic image of a vessel according to another embodiment of the present disclosure.
Figure 11:
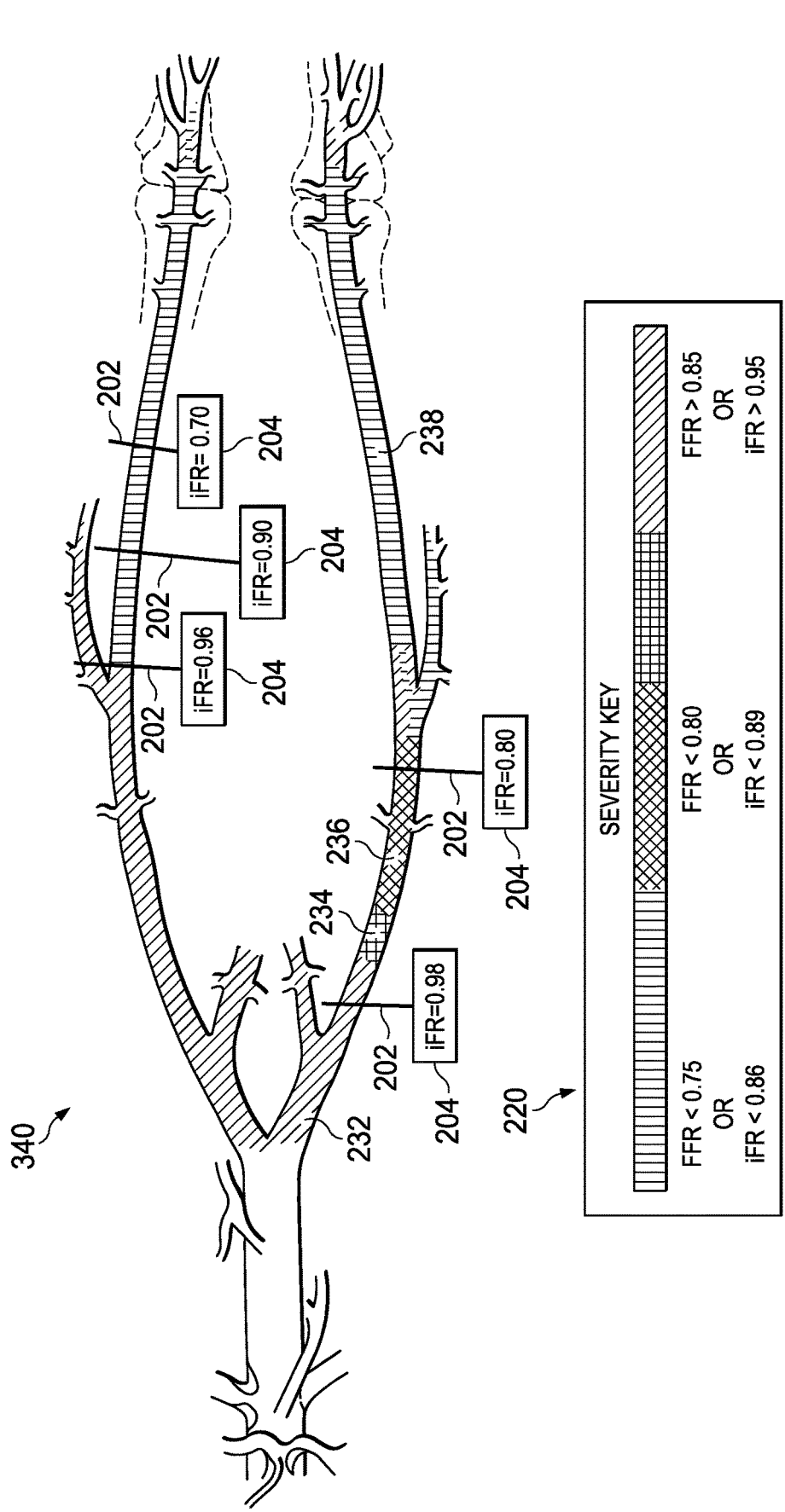
FIG. 11 is an annotated version of a stylized image of a vessel according to another embodiment of the present disclosure.
Figure 12:
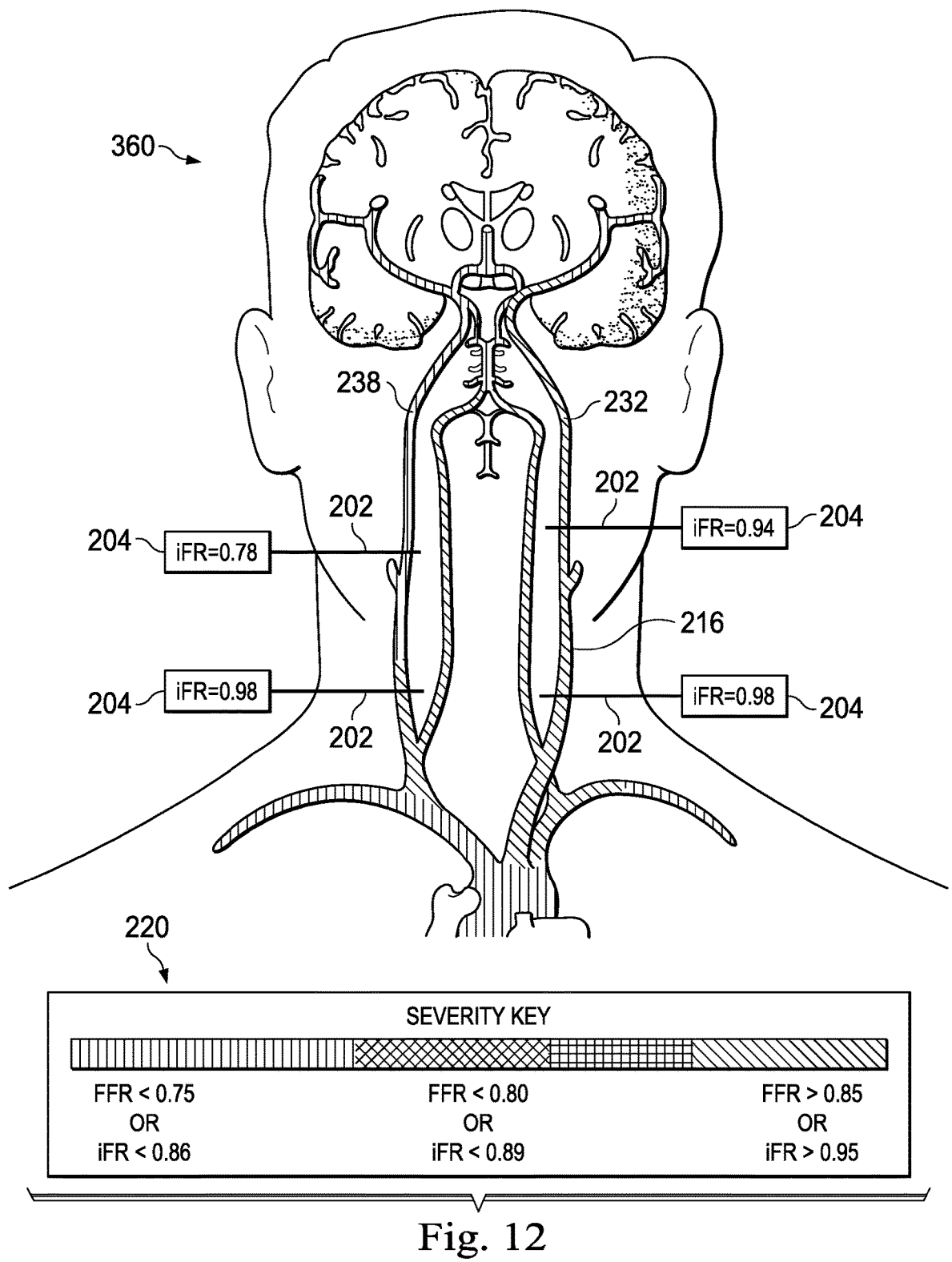
FIG. 12 is an annotated version of a stylized image of a vessel according to another embodiment of the present disclosure.

The discussion below generally refers to FIGS. 5-12. FIGS. 5, 7, 8, 11, and 12 are annotated versions of stylized images of a vessel according to embodiments of the present disclosure. FIG. 5 includes a stylized image 200 of one or more coronary arteries. FIG. 7 includes stylized images 240 and 260 of one or more coronary arteries. FIG. 8 is a stylized image 280 of one or more coronary arteries. FIG. 11 includes a stylized image 340 of one or more peripheral arteries. FIG. 12 includes a stylized image 360 of one or more cerebrovascular vessels. FIGS. 9 and 10 are annotated versions of angiographic images of one or more coronary arteries according to embodiments of the present disclosure. FIG. 6 is a visual depiction of an index 220 for assessing the severity of one or more lesions and/or stenoses according to an embodiment of the present disclosure. FIGS. 5 and 7-12 also include index 220. FIGS. 5-12 can be displayed on a display of system assessing a patient's vasculature. That is, one or more components (e.g., a processor and/or processing circuit) of the system can provided display data to cause the display of the images shown in FIGS. 5-12.

The images of vessels in FIGS. 5 and 7-12 are annotated with one or more visualizations configured to assist in identifying one or more lesions and/or stenoses, and/or assess the severity thereof. The visualizations are based on physiology values obtained from an instrument (e.g., instrument 130) as the instrument is moved through the vessel. The vessels of FIGS. 5 and 7-12 can be colorized and/or otherwise visualized using a heat map that illustrates changes in pressure measurements obtained as the instrument is moved through the vessel. In that regard, in some instances the pressure measurements shown in the heat map are representative of a pressure differential between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances. In that regard, in some embodiments a diagnostic window is selected using one or more of the techniques described in U.S. Patent Publication No. 2013/0046190 A1, published on Feb. 21, 2013 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the physiology values (e.g., pressure differential measurements) depicted in FIGS. 5 and 7-12 are configured based on the threshold value. FIG. 6 is an index or severity key 220 showing the colors 222 and their corresponding physiological values 224. For example, a first color (e.g., green, medium grey, or otherwise) is utilized to represent values well above the threshold value (e.g., where the threshold value is 0.80 on a scale of 0.00 to 1.00, values above 0.85), a second color (e.g., yellow, white, or otherwise) is utilized to represent values near but above the threshold value (e.g., where the threshold value is 0.80 on a scale of 0.00 to 1.00, values between 0.82 and 0.84), a third color (e.g., orange, light grey, or otherwise) is utilized to represent values near the threshold value (e.g., where the threshold value is 0.80 on a scale of 0.00 to 1.00, values between 0.79 and 0.81), and a fourth color (e.g., red, dark grey, or otherwise) is utilized to represent values equal to or below the threshold value (e.g., where the threshold value is 0.80 on a scale of 0.00 to 1.00, values of 0.79 and below).

Area 232 of FIGS. 5-12 indicates parts of the vessel with low severity (e.g., areas with a relatively high FFR value). Area 234 indicates parts of the vessel with greater severity compared to area 232 (e.g., areas with a moderately high FFR value). Area 236 indicates parts of the vessel with a moderate severity (e.g., areas with a moderately low FFR value). Area 238 indicates parts of the vessel with a high severity (e.g., areas with a low FFR value). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

In some embodiments, the heat map included in FIGS. 5 and 7-12 is based on a cumulative or total pressure differential, where the color selected for a particular point is determined based on the pressure differential between the instrument at that point being moved through the vessel and the stationary or fixed instrument. In other embodiments, the heat map is based on localized pressure differential, where the color selected for a particular point is determined based on differences between the pressure differential of that point with one or more of the surrounding points. In that regard, the localized pressure differential is calculated as the difference between the immediately preceding point in some instances. For example, the localized pressure differential for point $P_n$ is equal to the cumulative or total pressure differential for point $P_n$ minus the total or cumulative pressure differential for point $P_{n-1}$. In other instances, the localized pressure differential is calculated as the difference between that point and a point a fixed amount of time (e.g., 10 ms, 5 ms, 2 ms, 1 ms, or otherwise) or distance (e.g., 10 mm, 5 mm, 2 mm, 1 mm, or otherwise) away from that point. By utilizing a localized pressure differential the location of significant changes in pressure differential values, which are often associated with the presence of a lesion or stenosis, can be identified.

FIGS. 5 and 7-12 includes transition points or areas of the vessel wherein the physiology values between portions of the vessel change by a threshold amount. In some embodiments, the threshold amount can be fixed, while in other embodiments, the threshold amount can vary between patients. The one or more transition points can be indicated by visualizations. In FIGS. 5 and 7-12, the visualizations are markings 202. Markings 202 can be described as tick marks. In some embodiments, markings 202 can extend transversely across the vessel. In other embodiments, markings 202 can take different shapes (e.g., circles, squares, etc.), be in different positions relative to the vessel (beside, within, etc.), be differently sized, etc. The transition points can be representative of a boundary of a lesion or stenosis of the vessel that results in an increased or decreased pressure differential, which is illustrated by the change in color of the vessel. As a result, one or more visualizations (e.g., the change in color, markings 202, etc.) can be utilized to both identify the location of the lesion or stenosis within the vessel and assess the severity of the lesion or stenosis.

FIGS. 5 and 7-12 include visualizations for providing diagnostic information collected by one or more instruments at a corresponding location of the vessel on the display. In that regard, value indicators 204 can be disposed adjacent to markings 202 to indicate the location within the patient's vasculature to which the measurement corresponds. In other embodiments, value indicators 204 are displayed further away from markings 202, but an additional visual element (e.g., an arrow, a straight line, a curved line, marking 202 and value indicator 204 are the same or similar colors, etc.) is provided to indicate the location of the measurement. In some embodiments, the value indicators 204 include only the value of the physiological measurement (e.g., "0.96"), while in other embodiments, the value indicators 204 include the value and type of physiological measurement (e.g., "0.95 FFR"). In yet other embodiments, additional information, such as the time the measurement was taken, severity of the stenosis or lesion, etc. can also be provided. For example, a user may provide a user input (e.g., a selection from a drop-down menu, toggle through the available options, etc.) selecting the types of information that should be displayed in value indicators 204. Labels 206, for each of the value indicators 204, can also be provided. Labels 206 can include alphabetical, numeric, and/or other symbolic characters. Labels 206 may assist in identifying markings 202 and/or value indicators 204 (e.g., to distinguish between different markings/value indicators and/or to facilitate discussion of the vessel depictions).

In some embodiments, markings 202 and/or value indicators 204 can be positioned automatically. The system can be configured to select locations within the vessel that are clinically significant based on the diagnostic information (e.g., locations where the physiology value changes significantly). In some embodiments, markings 202 can be moved along the length of the vessel. For example, a user may provide a user input (e.g., click and drag the marking, click the marking to select it and then click a new location to which it should move, etc.) to cause movement of the markings 202. Value indicators 204 may be correspondingly updated with data that is based on the new location and/or move based on new location. That is, value indicators 204 can display diagnostic information along the length of the vessel. In this manner, a user may select a region of interest of the vessel by moving marking 202 and/or value indicator 204 to indicate an area of a vessel with a higher pressure differential, a lesion, and/or stenosis.

In some embodiments, visualizations to indicate a region of interest include multiple markings and a connector between the markings. For example, markings 210 and 212 of FIG. 7 are joined by connector 208. In some embodiments, markings 210 and 212 may be individually moved and connector 208 corresponding lengthens or shortens to span the space between them. In other embodiments, markings 210 and 212 and connector 208 are collectively translated along the vessel. Moving marking 210 in a direction along the vessel away from marking 212 may cause marking 212 to move away from marking 210 and cause connector 208 to lengthen. Moving marking 210 in a direction along the vessel towards markings 212 may cause marking 212 to move towards marking 210 and cause connector 208 to shorten. Movement of marking 212 may cause similar movement by marking 210.

The one or more visualizations of FIGS. 5 and 7-12 can include labels 214 and/or labels 216 for various predefined segments of the patient's vasculature. Labels 216 can be textual indications providing the names of major and/or minor vessels or segments thereof. Labels 214 can include alphabetical, numeric, and/or other symbolic characters. In some embodiments, labels 214 can correspond to a listing of parts of patient's vasculature. For example, labels 214 can be based on parts of the patient's vasculature identified by one or more risk calculators. The segments identified by labels 214 and/or 216 include, but are not limited to, right coronary artery (RCA), left main coronary artery, circumflex coronary artery, left anterior descending (LAD), RCA proximal, RCA mid, RCA distal, LAD proximal, LAD mid, LAD apical, first diagonal, additional first diagonal, second diagonal, additional second diagonal, proximal circumflex, intermediate/anterolateral, obtuse marginal, distal circumflex, left posterolateral, posterior descending, among others.

One or more images of a vessel, the visualizations in those images, and/or the measured physiological values can be used to evaluate whether and/or how to perform a surgical procedure. For example, the surgical procedure can be a CABG or PCI. For CABG planning, the measured physiological values and/or the images of the vessels, which indicate the location, extent, and severity of one or more lesions or stenoses, can be used to predict probabilities of graft patency and perfusion change. The regions of interest can be used to determine how and/or where in the vasculature to intervene. For PCI planning, the measured physiological values can be obtained using a guide catheter and/or a guide wire of calibrated and known lengths. Thus, the location, extent, and severity of one or more lesions or stenoses, can be used to estimate the number of stents, the length of stents, etc. The physiological values can also be used to calculate a numerical or otherwise objective indication of risk/benefit, as described herein. The objective indication of risk/benefit can be used to evaluate whether and/or how to perform a surgical procedure.

The one or more visualizations of FIGS. 5-12 can include or be supplemented with information regarding characteristics of the lesion or stenosis and/or the vessel using one or more other vessel data-gathering modalities. The other representations of the lesion or stenosis and/or the vessel can include, e.g., IVUS (including virtual histology), OCT, ICE, Thermal, Infrared, flow, Doppler flow, and/or other vessel data-gathering modalities. The additional information can provide a more complete and/or accurate understanding of the vessel characteristics and/or assist in evaluating a risk associated with a lesion or stenosis. For example, in some instances the information can include the occlusive value of the vessel. The occlusive value of the vessel and/or other additional information may be utilized to calculate an objective measure of the risk associated with the stenosis or lesion.

It is understood that numerous other visualization techniques may be utilized to convey the information of FIGS. 5-12 in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters.

The images of vessels in FIGS. 5 and 7-12 can include three-dimensional, two-dimensional, angiographic, a computed tomography angiographic (CTA), and/or other suitable forms of images. In some embodiments, a three-dimensional image may be rotated about a vertical axis. In some embodiments, a two-dimensional image may include multiple views about a vertical axis such that different two-dimensional views are shown when the image is rotated. In some implementations, the three dimensional model is displayed adjacent to a corresponding two dimensional depiction of the vessel. In that regard, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults.

While the visual representations of FIGS. 5-12 have been described separately, it is understood that a system may display any combination of these visual representations in series, simultaneously, and/or combinations thereof. In some instances, a system provides the user the ability to select which individual visual representation and/or combination of visual representations will be displayed.

Figure 13:
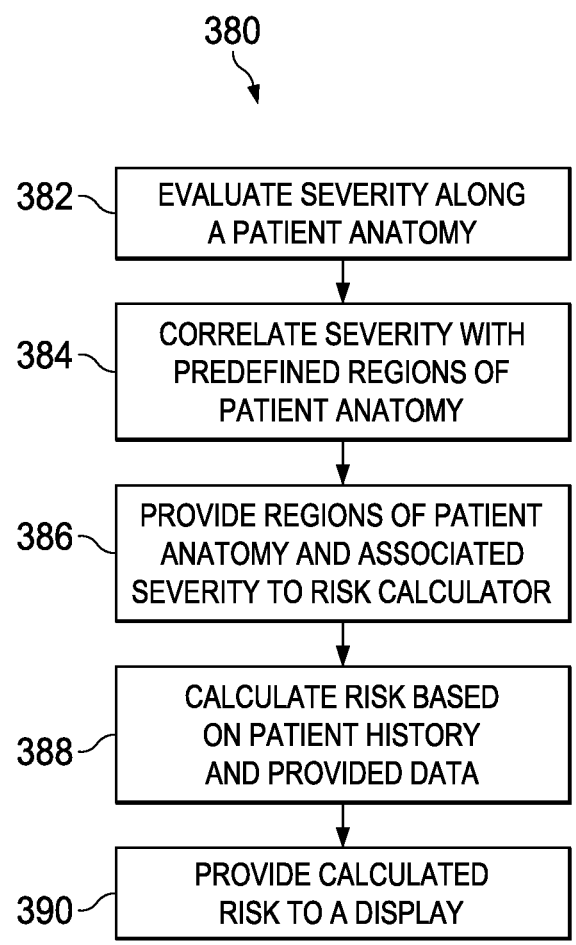
FIG. 13 is a flow diagram of a method of assessing risk according to an embodiment of the present disclosure.

FIG. 13 is a flow diagram of a method 380 for assessing risk according to an embodiment of the present disclosure. Method 380 can be implemented by a system described herein. At step 382, method 380 includes evaluating the severity of a lesion or stenosis along a patient anatomy. One or more diagnostic measurements (e.g., pressure-based including FFR and iFR, flow-based including CFR, etc.) can be used to characterize the existence and/or severity of a lesion. For example, when FFR is used, areas of a patient's vasculature that have a relatively high FFR (e.g., greater than 0.80) are characterized as not having a lesion or stenosis, while areas with a relatively low FFR (e.g., less than 0.80) are characterized as having a lesion or stenosis. The severity can be evaluated based on the heat map described herein.

At step 384, method 380 includes correlating the determined severity with predefined regions of the patient anatomy. The predefined regions of anatomy may correspond to the labels 214 used to identify segments of a patient's vasculature. For example, the RCA proximal segment may have a high severity due to a lesion or stenosis, while the LAD proximal segment may have a low severity because no lesion or stenosis is present. At step 386, the regions of the patient anatomy and associated severity are provided to a risk calculator. In various embodiments, the risk calculator can include one or more algorithms for calculating the likelihood of mortality, the likelihood of success when treating the lesion or stenosis, etc. The risk calculator may output a quantity that is an objective measure of the risk associated with the patient's condition. The risk calculator may include a fractional flow reserve (FFR)-guided SYNTAX score (SS) or functional SYNTAX score (FSS), as described in Chang-Wook Nam, et al., *Functional SYNTAX Score for Risk Assessment in Multivessel Coronary Artery Disease*, Journal of the American College of Cardiology 2011; 58(12): 1211-1218, which is incorporated by reference herein in its entirety. The risk calculator may also include any modified SYNTAX score or any numerical or otherwise objective risk score that incorporates physiologic measurements, including, but not limited to, flow-based (CFR, etc.) and/or pressure-based (FFR, iFR, etc.) parameters. The risk calculator may also generate an indication of perfusion benefit and an indication of graft patency. For example, the risk calculator may quantify the predicted perfusion change should CABG be selected as the revascularization strategy.

At step 388, method 380 includes calculating the risk score based on the provided data and any additional relevant patient history. The provided data and/or patient history can be a binary (e.g., yes or no) or continuous (e.g., percentage of narrowing of the vessel). The provided data may be based on measured diagnostic information (as evaluated in step 382). The provided data can include one or more of existence of mitral stenosis, existence of aortic stenosis, existence of total occlusion, existence of trifurcation and how many diseased segments involved, existence of bifurcation, existence of aorto ostial lesion, existence of severe tortuosity in the vessel, whether length of the lesion is greater than 20 mm, existence of heavy calcification, existence of thrombus, if and which segments are diffusely diseased and/or narrowed, number of lesions, percentage of narrowing, involvement of proximal LAD lesion, etc. Other relevant patient history can include one or more of age; gender; whether the patient has diabetes, hypertension, hypercholesterolemia, peripheral vascular disease; whether the patient is currently smoking; whether the patient has a positive family history of heart disease; whether the patient has had a previous myocardial infarction and/or previous PCI; the ventricular ejection fraction percentage, etc. At step 390, the method 380 includes providing the calculated risk to a display. In some implementations, calculating a risk score includes providing the physiology measurements into an algorithm for predicting the benefits of perfusion resulting from placement of a coronary bypass graft.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of providing information of a vessel of a patient to assist in evaluating the vessel, comprising:
    obtaining pressure measurements from a pressure-sensing instrument and a pressure-sensing guidewire while the pressure-sensing guidewire is moved longitudinally through the vessel from a first position to a second position and the pressure-sensing instrument remains stationary within the vessel;
    calculating, based on the pressure measurements from the pressure-sensing instrument and the pressure-sensing guidewire, a plurality of pressure ratios along the vessel;
    defining a plurality of regions of the vessel based on a comparison of the plurality of pressure ratios with a threshold value such that each region of the plurality of regions comprises a respective severity;
    automatically determining a first location at a border of two regions of the plurality of regions having different severities;

outputting an image of the plurality of regions of the vessel on a display, wherein the image comprises a two-dimensional angiographic image, the image including:
  a visualization of the respective severity for the two regions,
  a marking of the first location at the border of the two regions, and
  an indicator displaying a numerical value of a first pressure ratio of the plurality of pressure ratios corresponding to the first location;
receiving a user input moving the marking to a second location along the vessel; and
outputting a modified image including the indicator displaying a numerical value of a second pressure ratio of the plurality of pressure ratios corresponding to the second location.

2. The method of claim 1, wherein comprising:
receiving a user input moving the indicator to a third location along the vessel; and
outputting an additional modified image including the indicator displaying a numerical value of a third pressure ratio of the plurality of pressure ratios corresponding to the third location.

3. The method of claim 1, wherein the visualization of the respective severity includes a heat map representative of one or more pressure ratios of the plurality of pressure ratios.

4. The method of claim 3, wherein a first visual characteristic of the heat map is associated with pressure ratios of the one or more pressure ratios that are above a threshold value and a second visual characteristic of the heat map is associated with pressure ratios of the one or more pressure ratios that are below the threshold value.

5. The method of claim 4, wherein the first visual characteristic of the heat map is a first color and the second visual characteristic of the heat map is a second color visually distinguishable from the first color.

6. The method of claim 1, wherein the image is an extravascular image.

7. The method of claim 6, wherein the extravascular image is a computed tomography angiographic (CTA) image.

8. The method of claim 1, further comprising:
calculating a risk score associated with the pressure measurements; and
outputting the risk score on the display, the risk score associated with at least one of the plurality of regions.

9. The method of claim 8, wherein calculating the risk score includes:
providing the pressure measurements to a risk calculator, wherein the risk calculator includes a calculator for determining at least one of a SYNTAX score, a fractional flow reserve (FFR)-guided SYNTAX score (functional SYNTAX score), an indication of perfusion benefit, or an indication of graft patency; and
calculating the risk score with the risk calculator using at least one of the physiology pressure measurements or a patient history.

10. A system for providing information of a vessel of a patient to assist in evaluating the vessel, comprising:
a pressure-sensing guidewire sized and shaped for introduction into the vessel of the patient;
a processing system in communication with the pressure-sensing guidewire and a pressure-sensing instrument sized and shaped for introduction into the vessel of the patient, the processing system configured to:
  obtain pressure measurements from the pressure-sensing instrument and the pressure-sensing guidewire while the pressure-sensing guidewire is moved longitudinally through the vessel of the patient from a first position to a second position while the pressure-sensing instrument is maintained in a fixed longitudinal position with respect to the vessel;
  calculate, based on the pressure measurements from the pressure-sensing instrument and the pressure-sensing guidewire, a plurality of pressure ratios along the vessel; and
  define a plurality of regions of the vessel based on a comparison of the plurality of pressure ratios with a threshold value such that each region of the plurality of regions comprises a respective severity;
  automatically determine a first location at a border of two regions of the plurality of regions having different severities;
  output an image of the plurality of regions of the vessel on a display in communication with the processing system, wherein the image comprises a two-dimensional angiographic image, the image including:
    a visualization of the respective severity for the two regions,
    a marking of the first location at the border of the two regions, and
    an indicator displaying a numerical value of a first pressure ratio of the plurality of pressure ratios corresponding to the first location;
  receive a user input moving the marking to a second location along the vessel; and
  output a modified image including the indicator displaying a numerical value of a second pressure ratio of the plurality of pressure ratios corresponding to the second location.

11. The system of claim 10, the processing system further configured to:
receive a user input moving the indicator to a third location along the vessel; and
output an additional modified image including the indicator configured to display a numerical value of a third pressure ratio of the plurality of pressure ratios corresponding to the third location.

12. The system of claim 10, wherein the visualization of the respective severity includes a heat map representative of one or more pressure ratios of the plurality of pressure ratios.

13. The system of claim 12, wherein a first visual characteristic of the heat map is associated with pressure ratios of the one or more pressure ratios that are above a threshold value and a second visual characteristic of the heat map is associated with pressure ratios of the one or more pressure ratios that are below the threshold value.

14. The system of claim 12, wherein the first visual characteristic of the heat map is a first color and the second visual characteristic of the heat map is a second color visually distinguishable from the first color.

15. The system of claim 10, wherein the image is an extravascular image.

16. The system of claim 15, wherein the extravascular image is a computed tomography angiographic (CTA) image.

17. The system of claim 10, wherein the processing system is further configured to:
calculate a risk score associated with the pressure measurements; and
output the risk score on the display, the risk score associated with at least one of the plurality of regions.

18. The system of claim 17, wherein the processing system, to calculate the risk score, is configured to:
provide the pressure measurements to a risk calculator, wherein the risk calculator includes a calculator for determining at least one of a SYNTAX score, a fractional flow reserve (FFR)-guided SYNTAX score (functional SYNTAX score), an indication of perfusion benefit, or an indication of graft patency; and
calculate the risk score with the risk calculator using at least one of the pressure measurements or a patient history.

19. The system of claim 10, wherein the image includes, for two or:
an additional indicator displaying a numerical value of a pressure ratio of the plurality of pressure ratios for each of the two regions.

20. The system of claim 10, further comprising:
the pressure-sensing instrument.

21. The system of claim 10, wherein the marking comprises a first marking, and wherein the image further comprises:
a second marking positioned at a third location spaced from the first location; and
a connector extending between the first marking and the second marking,
wherein the processing system is further configured to determine a distance between the first marking and the second marking.

22. The system of claim 10,
wherein the marking comprises a first marking,
wherein the image further comprises:
a second marking positioned at a third location in the vessel,
an additional indicator displaying a numerical value of a third pressure ratio of the plurality of pressure ratios corresponding to the third location of the vessel, and
wherein the processing system is configured to output, based on the received user input moving the first marking to the second location, the modified image, wherein the modified image comprises:
the first marking positioned at the second location;
the indicator displaying a numerical value of the second pressure ratio corresponding to the second location;
the second marking positioned at the third location in the vessel; and
the additional indicator displaying the numerical value of the third pressure ratio corresponding to the third location of the vessel.

23. The system of claim 10, wherein the vessel comprises a plurality of anatomical segments, wherein the image includes a segment identifier indicating an anatomical segment among the plurality of anatomical segments.

* * * * *